US00PP16572P3

(12) United States Plant Patent
Carruth

(10) Patent No.: US PP16,572 P3
(45) Date of Patent: May 23, 2006

(54) HYBRID TEA ROSE PLANT NAMED 'WEKBLUNEZ'

(50) Latin Name: *Rosa hybrida*
Varietal Denomination: WEKblunez

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 156 days.

(21) Appl. No.: 10/916,005

(22) Filed: Aug. 10, 2004

(65) Prior Publication Data

US 2006/0037114 P1 Feb. 16, 2006

(51) Int. Cl.
*A01H 5/00* (2006.01)

(52) U.S. Cl. ..... Plt./137

(58) Field of Classification Search ..... Plt./137, Plt./138, 130, 148

See application file for complete search history.

*Primary Examiner*—Howard J. Locker
(74) *Attorney, Agent, or Firm*—Christie, Parker & Hale, LLP

(57) ABSTRACT

A new variety of hybrid tea rose suitable for garden decoration, having flowers of orchid pink coloration.

1 Drawing Sheet

Classification: The present invention relates to a new *Rosa hybrida* plant, WEKcryplag×MACgenev.

Variety denomination: The new plant has the varietal denomination 'WEKblunez'.

BACKGROUND OF THE INVENTION

This invention relates to a new and distinct variety of Hybrid Tea Rose. It has as its seed parent the variety known as 'WEKcryplag' (U.S. Plant Pat. No. 10,072) and as its pollen parent the variety known as 'MACgenev' (U.S. Plant Pat. No. 8,279).

SUMMARY OF THE INVENTION

Among the features which distinguish the new variety from other presently available and commercial rose cultivars known to the inventor are the following combination of characteristics: its very fragrant flowers, its pink styles that suffuse to red as the flowers age, its very low thorned shoots and branches and its very well foliated plant. The plant has an upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKblunez' may be asexually propagated by budding and grafting. The budding and grafting successfully occurred on the plant/rootstock *Rosa hybrida* cv. 'Dr. Huey'.

COMPARISON WITH PARENTS

The new rose may be distinguished from its seed parent, 'WEKcryplag' by the following combination of characteristics: whereas 'WEKblunez' bears very double flowers (about 28 to 52 petals) of orchid pink coloration, 'WEKcryplag' bears semi-double flowers with significantly lesser petalage (about 12 to 16 petals) of clear lavender coloration. The new variety is classified as a hybrid tea rose with a upright medium height mature growing habit, whereas the seed parent is classified as a floribunda rose with a significantly smaller, lower and rounded to more spreading mature growing habit.

The new variety may be distinguished from its pollen parent, 'MACgenev' by the following combination of characteristics: whereas 'WEKblunez' bears flowers of orchid pink coloration, 'MACgenev' bears flowers of soft coral pink coloration. The pollen parent bears glossy foliage, whereas the new variety bears semi-glossy foliage. 'WEKblunez' usually bears no large or small prickles on the branches or the new shoots, whereas 'MACgenev' bears some large prickles and few small prickles on its branches and new shoots.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of July. Phenotypic expression may vary with environmental, cultural and climatic conditions, as well as diffferences in conditions of light and soil.

FLOWER

The new variety usually bears its flowers singly. Flowers are borne on strong medium to long stems (about 36 to about 76 cm.). Outdoors, the plant blooms abundantly and nearly continuously during the growing season. The flowers have a strong old rose fragrance.

BUD

The peduncle is about 2.8 to about 6.0 cm. in length, of average to heavy caliper (about 0.2 to about 0.5 cm. in diameter), and usually erect and somewhat stiff. It is entirely smooth, without stipitate glands, hairs or prickles. Peduncle color is between 146C and 146A sometimes very lightly suffused, especially on the side exposed to the sun, with near 183D.

Before the calyx breaks, the bud is about 1.4 to about 2.2 cm. in diameter at the widest point, about 1.6 to about 2.5 cm. in length, and globular to somewhat ovoid in shape. The surface of the bud bears some foliaceous appendages, usually with stout somewhat cut foliaceous parts extending beyond the tip of the bud about ½ or more of its length. Bud color is between 146B and 146A.

The sepals are about 2.0 to about 4.9 cm. in length and about 0.7 to about 1.2 cm. in width at the widest point. The outer surface color of the sepal is between 146B and 146A. The inner surface color of the sepal is between 144C and 147A and covered with fine wooly tomentum; sepal margins are lined with many stipitate glands and hairs.

As the petals open (after the calyx breaks), the bud is about 2.0 to about 3.6 cm. in diameter at the widest point, about 2.0 to about 3.2 cm. in length, and very globular in form. The color of the under surfaces of the newly opened petals is between 54A and 56A sometimes with pigmentation as dark as between 60A and 59A mostly toward the edge of the petal. At the point where the petal attaches, there is a moderately small zone of between 4D and 2D. The color of the upper surfaces of the newly opened petals is between 49C and 62D sometimes with pigmentation as dark as between 60A and 59A mostly toward the edge of the petal. At the point where the petal attaches, there is a moderately small zone between 4D and 2D.

BLOOM

When fully open, the bloom ranges from about 10.0 to about 12.2 cm. in diameter. Petalage is very double with about 28 to 52 petals and about 5 to 22 petaloids irregularly arranged. When partially open, the bloom form is high centered to somewhat globular, and the petals are moderately tightly spiraled to slightly cupped with petal edges moderately reflexed outward. When fully open, the bloom form is more cupped, and the petals are loosely cupped with petal edges moderately reflexed outward.

PETALS

The substance of the petals is somewhat heavy to leathery and of somewhat thin to medium thickness, with upper surfaces slightly shiny and under surfaces somewhat shiny to matte. The outer petals are broadly obovate to round in shape with rounded apices and sometimes notched with one notch. The inner petals are nearly round to moderately obovate in shape with rounded apices and sometimes notched with one notch. The petals are about 2.3 to about 6.2 cm. in length and about 1.8 to about 6.3 cm. in width at the widest point. Petal margins are entire to sometimes moderately crenate especially on the outermost petals edges.

NEWLY OPENED FLOWER

The under surface color of the outer petals is between 62C and 56B. At the point where the petal attaches, there is a moderately small zone of between 4D and 2D. The upper surface color of the outer petals is irregularly shaded with as light as between 62D and 56D to as dark as between 64D and 56A. At the point where the petal attaches, there is a moderately small zone of between 2D and 3D.

The under surface color of the intermediate and inner petals is between 61D and 56A. The upper surface color of the intermediate and inner petals is between 62B and 56A.

The general tonality of the newly opened flower is between 62B and 56A.

THREE-DAY-OLD FLOWER

The under surface color of the outer petals is between 62D and 56C. At the point where the petal attaches, there is a moderately small zone of between 4D and 2D. The upper surface color of the outer petals is irregularly shaded with as light as between 56C and 56D to as dark as between 64D and 56B. At the point where the petal attaches, there is a moderately small zone of between 2D and 4C.

The under surface color of the intermediate and inner petals is between 65C and 62C. The upper surface color of the intermediate and inner petals is irregularly shaded with as light as between 56B and 56C to as dark as between 64D and 56A.

The general tonality of the three-day-old flower is irregularly shaded with as light as between 56B and 56C to as dark as between 64D and 56A.

On the spent bloom, the petals usually drop of cleanly.

In July in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (average about 120) and are arranged regularly about the pistils; some are mixed with petaloids. The filaments are of medium to long length (about 0.5 to about 1.1 cm.), most with anthers. Filaments are between 3C and 5C at the base suffusing to between 4D and 2D in color near the top. The anthers are somewhat small for the class and all open approximately at the same time. Anther color is between 22A and 16D when immature and between 161C and 166B at maturity. Pollen is abundant.

FEMALE REPRODUCTIVE ORGANS

Pistils vary in number (average about 210). The styles are moderately even, average in length (about 0.4 to about 0.7 cm.), somewhat thin in caliper, and moderately separated to somewhat columnar. Stigma color is between 10C and 8C. Style color is near 4D often moderately suffused near the top with between 53C and 53D. The suffusion intensifies as the flowers ages to between 187A and 187B. Ovaries are usually all enclosed in the calyx.

Hips are of average length (about 2.7 to about 3.3 cm.), moderately obovate in form and somewhat flat at the top, and between 21A and 17B in color when ripe. The hip surface is smooth with thick fleshy walls. The sepals are fugacious and straight in shape. The seeds are irregularly rounded, smooth in texture, approximately 35 to about 50 per hip, about 0.4 to about 0.7 cm. in diameter at the widest point and between 161C and 164D in color.

FOLIAGE

The compound leaves are usually comprised of three to five or more leaflets and are borne abundantly. The five-leaflet leaves are about 11.2 to about 15.8 cm. in length and about 11.6 to about 15.6 cm. in width at the widest point, moderately leathery to somewhat crisp in texture, and semi-glossy in finish. The terminal leaflets are about 4.6 to about 10.1 cm. in length and about 3.6 to about 5.5 cm. in width at the widest point, shaped oval to somewhat ovate with acute apices and moderately round to somewhat acute bases. Their margins are simply serrate.

The upper surface color of the mature leaf is between 147A and 146A. The under surface color of the mature leaf is between 147B and 146B. The upper surface color of the young leaf is between 146A and 144C, sometimes moderately suffused with between 187A and 183A. The under surface color of the young leaf is between 146B and 144C, sometimes moderately suffused with between 187A and 183A.

The rachis is average to somewhat heavy in caliper and somewhat smooth. The upper side is moderately grooved with few hairs and stipitate glands on the edges of the grooves. The under side of the rachis is somewhat smooth with very few stipitate glands and small prickles. The rachis color is between 144A and 146A sometimes suffused with between 187A and 183A.

The stipules are about 1.0 to about 1.5 cm. in length and of medium width (about 0.5 to about 0.8 cm.) with somewhat long straight points that usually turn out at an angle of more than 45 degrees and sometimes slightly recurve toward the stem. The stipules color is between 144A and 146A sometimes suffused with between 187C and 183C.

The petiole is about 0.6 to about 1.5 cm. in length and about 0.15 to about 0.2 cm in diameter at the widest point. The petiole color is between 144A and 146A sometimes suffused with between 187A and 183A.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has an upright medium height growing habit (about 138 to about 152 cm. in height and about 66 to about 83 cm. spread at the widest point), with full branching. It displays vigorous growth and the canes are of medium size caliper for the class.

The color of the major stems is between 146A and 146B. They bear some large prickles that are about 0.6 to about 1.1 cm. in length. The large prickles are almost straight and angled slightly downward with a short length broad rounded base; prickle color is between 166D and 165C . The major stem bears some small prickles of similar shape and coloration.

The color of the branches is between 144A and 146A. They usually bear no large or small prickles. Sometimes they bear few large prickles which are of similar size and shape to the large prickles on the major stems; prickle color is between 187B and 183B.

The color of the new shoots is between 144A and 146A sometimes lightly suffused with between 187C and 183C. They bear no large or small prickles.

I claim:

1. A new and distinct hybrid tea rose plant of the variety substantially as described and illustrated herein.

* * * * *

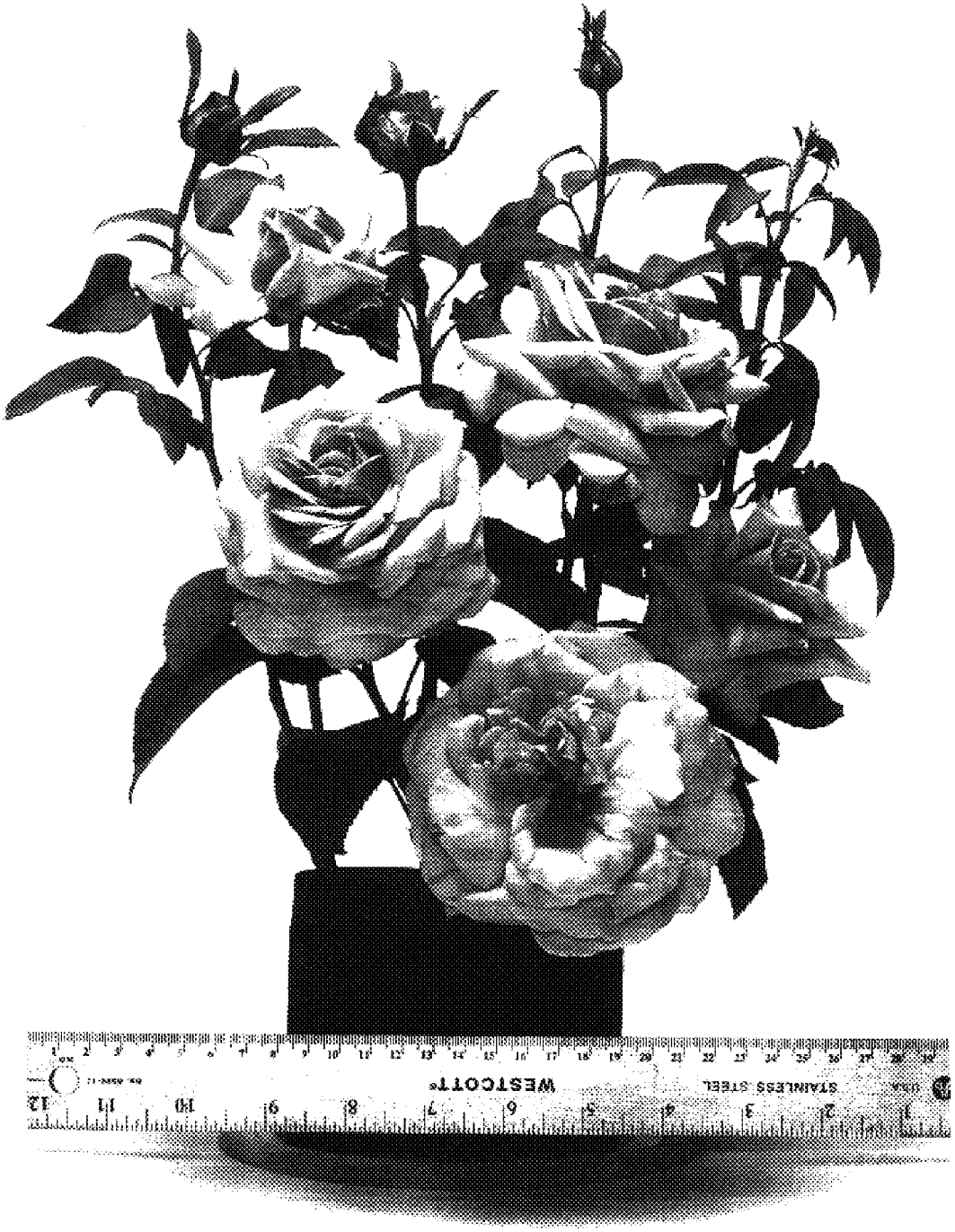
WESTCOTT
STAINLESS STEEL